(12) United States Patent
Malkowski et al.

(10) Patent No.: US 9,017,314 B2
(45) Date of Patent: Apr. 28, 2015

(54) SURGICAL ARTICULATION ASSEMBLY

(75) Inventors: Jaroslaw T. Malkowski, Trumbull, CT (US); Peter Hathaway, Lebanon, CT (US)

(73) Assignee: Covidien LP, Mansfield, MA (US)

( * ) Notice: Subject to any disclaimer, the term of this patent is extended or adjusted under 35 U.S.C. 154(b) by 415 days.

(21) Appl. No.: 13/478,182

(22) Filed: May 23, 2012

(65) Prior Publication Data

US 2012/0310220 A1 Dec. 6, 2012

Related U.S. Application Data

(60) Provisional application No. 61/492,047, filed on Jun. 1, 2011.

(51) Int. Cl.
*A61B 17/00* (2006.01)
*A61B 17/29* (2006.01)

(52) U.S. Cl.
CPC ........ *A61B 17/29* (2013.01); *A61B 2017/00314* (2013.01); *A61B 2017/00327* (2013.01); *A61B 2017/2908* (2013.01); *A61B 2017/2929* (2013.01)

(58) Field of Classification Search
CPC ............. A61B 2017/00314; A61B 2017/2908; A61B 17/00; A61B 2017/00327; A61B 2017/2929
See application file for complete search history.

(56) References Cited

U.S. PATENT DOCUMENTS

| | | |
|---|---|---|
| 4,898,577 A | 2/1990 | Badger et al. |
| 4,997,419 A | 3/1991 | Lakatos et al. |
| 4,998,916 A | 3/1991 | Hammerslag et al. |
| 5,007,434 A | 4/1991 | Doyle et al. |
| 5,441,483 A | 8/1995 | Avitall |
| 5,472,017 A | 12/1995 | Kovalcheck |
| 5,507,725 A | 4/1996 | Savage et al. |
| 6,068,621 A | 5/2000 | Balceta et al. |
| 6,923,813 B2 | 8/2005 | Phillips et al. |
| 7,250,027 B2 | 7/2007 | Barry |
| 7,608,056 B2 | 10/2009 | Kennedy, II |
| 7,637,903 B2 | 12/2009 | Lentz et al. |
| 7,682,319 B2 | 3/2010 | Martin et al. |
| 7,811,277 B2 | 10/2010 | Boulais |
| 2003/0149422 A1 | 8/2003 | Muller |
| 2005/0014995 A1 | 1/2005 | Amundson et al. |
| 2005/0240193 A1 | 10/2005 | Layne et al. |
| 2007/0049966 A1 | 3/2007 | Bonadio et al. |
| 2007/0250110 A1 | 10/2007 | Lu et al. |
| 2007/0270679 A1 | 11/2007 | Nguyen et al. |
| 2008/0188869 A1 | 8/2008 | Weitzner et al. |
| 2009/0043299 A1 | 2/2009 | Racz |
| 2009/0192495 A1 | 7/2009 | Ostrovsky et al. |

(Continued)

*Primary Examiner* — Gary Jackson
*Assistant Examiner* — Scott T. Luan

(57) ABSTRACT

A surgical articulation assembly is disclosed, including a control assembly and an articulable portion. The surgical articulation assembly has a passage therethrough for receiving a surgical object. The articulable portion includes at least two segments capable of independent movement. Disposed within the control assembly is an actuation assembly including a driving member, a translating member, two engagement members, a rotating member, and connecting members engaging in cooperation to effect forces through the connecting members on each of the first and second segments. More than one actuation assembly may be present, and the associated components of the actuation assembly may be configured to effect bi-directional articulation of the first and second segments in more than one plane.

19 Claims, 13 Drawing Sheets

(56) References Cited

U.S. PATENT DOCUMENTS

| | | |
|---|---|---|
| 2009/0312696 A1 | 12/2009 | Copa et al. |
| 2010/0004591 A1 | 1/2010 | Barenboym et al. |
| 2011/0213363 A1* | 9/2011 | Cunningham et al. .......... 606/41 |
| 2012/0199632 A1* | 8/2012 | Spivey et al. .............. 227/176.1 |

* cited by examiner

SURGICAL ARTICULATION ASSEMBLY

CROSS-REFERENCE TO RELATED APPLICATIONS

This application claims the benefit of and priority to U.S. Provisional Patent Application No. 61/492,047, filed Jun. 1, 2011, the entire disclosure of which is incorporated by reference herein.

BACKGROUND

1. Technical Field

The present disclosure relates generally to a surgical device for use in a minimally invasive surgical procedure. More particularly, the present disclosure relates to an articulating surgical assembly having at least a first segment and a second segment that are separately movable.

2. Background of Related Art

A minimally invasive surgical procedure is one in which a surgeon enters a patient's body through one or more small openings in the patient's skin or a naturally occurring opening (e.g., mouth, anus, or vagina). As compared with traditional open surgeries, minimally invasive surgical procedures have several advantages and disadvantages. Minimally invasive surgeries include arthroscopic, endoscopic, laparoscopic, and thoracic surgeries. Advantages of minimally invasive surgical procedures over traditional open surgeries include reduced trauma and recovery time for patients.

However, some disadvantages include a lack of direct visualization of the surgical site and reduced dexterity of instruments, as compared to traditional open surgeries. Maneuvering surgical instruments with the necessary degree of dexterity for surgical procedures is difficult under these conditions, compounded by the fact that a surgeon often needs to reach off-axis points within a body cavity in the course of minimally invasive procedures. Accordingly, a need exists for a system capable of articulating surgical instrumentation through multiple planes in an internal body cavity with accuracy and precision. It is further desirable to provide a surgeon with a control system that is intuitive and easy to operate to compensate for the lack of direct visualization within a body cavity.

Accordingly, a need exists for a surgical device capable of giving a surgeon control of a surgical instrument in multiple planes of movement.

SUMMARY

A surgical articulation assembly is disclosed, including a control assembly and an articulable portion. The surgical articulation assembly has a passage therethrough for receiving a surgical object. The articulable portion includes at least two segments capable of independent movement.

The control assembly defines an axis and includes one or more actuation assemblies. Each actuation assembly includes a driving member having a threaded or otherwise textured surface. Circumferentially disposed around the driving member is a translating member that has a channel for engaging the surface of the driving member. A first engaging member is attached to a shoulder extending from the translating member, and translates proximally and distally along the driving member with the translating member as the driving member is rotated. A pulley is attached to an outer surface of each of the first and second engaging members.

The first engaging member has a surface that interengages a rotating member disposed within a housing of the control assembly. A second engaging member has a surface that interengages the surface of the rotating member, and is diametrically opposed to the first engaging member on the rotating member.

Connecting members that may be tensile or rigid elements couple the first and second engaging members and the pulleys to portions of the first and second segments of the articulable portion. Distal ends of the connecting members are disposed in portions of the first and second segments of the articulable portion such that upon rotation of the driving member and subsequent motion of first and second engaging members and pulleys, axial forces are transferred to the first and second segments of the articulable portion through the connecting members. A portion of the connecting members associated with the pulleys may be fixed to a portion of the control assembly or another surface of the surgical articulation assembly. The connecting members may be placed such that articulation is effected in multiple directions in multiple planes in each of the first and second segments of the articulable portion. The connecting members associated with the pulleys are configured to effect articulation at a different rate than the connecting members associated with the first and second engaging members. Also disclosed is a method of effecting articulation of a surgical object with the surgical access assembly.

In one embodiment, the first actuation assembly effects bi-directional articulation of the first segment and second segments in a first plane, and the second actuation assembly effects articulation of the first and second segments in a second plane, the second plane being substantially transverse to the first plane.

These and other features of the current disclosure will be explained in greater detail in the following detailed description of the various embodiments.

BRIEF DESCRIPTION OF THE DRAWINGS

Various embodiments of the present disclosure are described hereinbelow with reference to the drawings, wherein.

Figure 1:
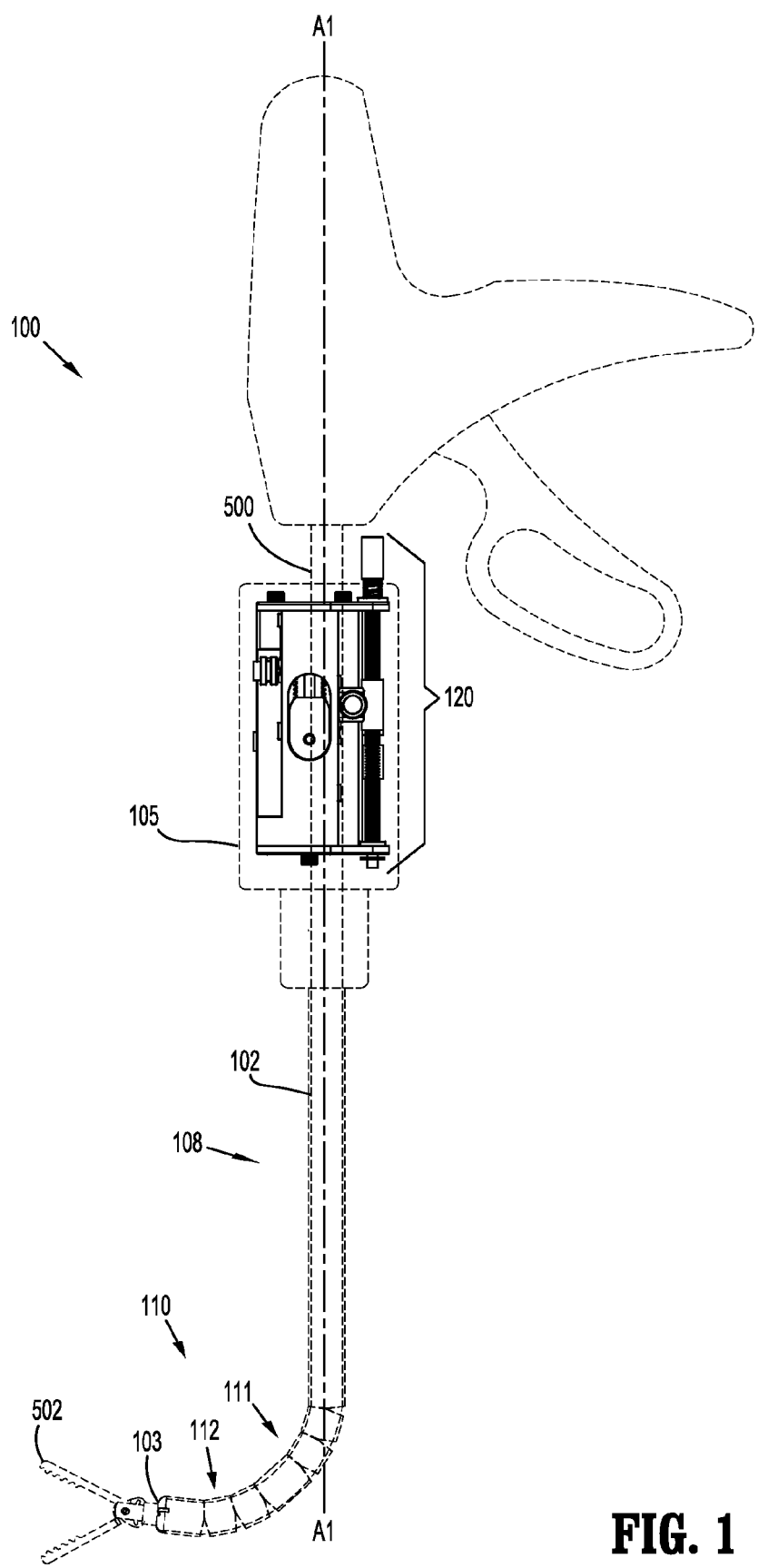
FIG. 1 is a perspective view of a surgical articulation assembly in accordance with the present disclosure, with a surgical object having an end effector inserted therethrough.

Other features of the present disclosure will become apparent from the following detailed description taken in conjunction with the accompanying drawings, which illustrate, by way of example, the principles of the present disclosure.

DETAILED DESCRIPTION OF THE EMBODIMENTS

Embodiments of the presently disclosed surgical access assemblies for use in minimally invasive surgery are described in detail with reference to the drawings, in which like reference numerals designate identical or corresponding elements in each of the several views. As used herein, the term "distal" refers to that portion of the tool or component thereof which is further from the user while the term "proximal" refers to that portion of the tool or component thereof which is closer to the user. The presently disclosed surgical access assemblies are usable in an opening through a patient's tissue, in a naturally occurring orifice (e.g. mouth, anus or vagina), or through an access member.

Referring initially to FIG. 1, a surgical articulation assembly 100 is shown. Surgical articulation assembly 100 includes a control assembly 120, which defines a longitudinal axis A1. Extending from the control assembly 120 is an elongate member 108 having an articulable portion 110.

Control assembly 120 may be disposed within an outer housing 105 (shown in phantom view). Outer housing 105 may have any suitable shape or profile to accommodate control assembly 120, and may include an aperture to receive elongate member 108 and articulable portion 110. The housing may sealably engage the elongate member 108 through the aperture, or outer housing 105 and elongate member 108 may be press fit, threaded, adhered, secured with a bayonet-type coupling, or utilize a securing member such as a clamping collar. Articulable portion 110 includes at least a first segment 111 and a second segment 112. Second segment 112 is disposed distally of the first segment 111. The first segment 111 and second segment 112 are capable of independent movement relative to the longitudinal axis A1 and to each other, as will be discussed further below.

Surgical articulation assembly 100 has a passage 102 therethrough to receiving a surgical object 500. Surgical object 500 may be inserted through the passage 102 through the surgical articulation assembly 100, and may engage the outer housing 105. Surgical articulation assembly 100 allows user-controlled articulation of the surgical object 500 inserted therethrough. Accordingly, surgical object 500 is an instrument capable of flexion within an articulating member, such as graspers, forceps, probes, scalpels, or staplers, and includes an end effector 502, shown extending through a distal end 103 of the passage 102. It is also contemplated that the surgical object 500 and elongate member 108 may be inserted through an access member (not shown).

Figure 4:
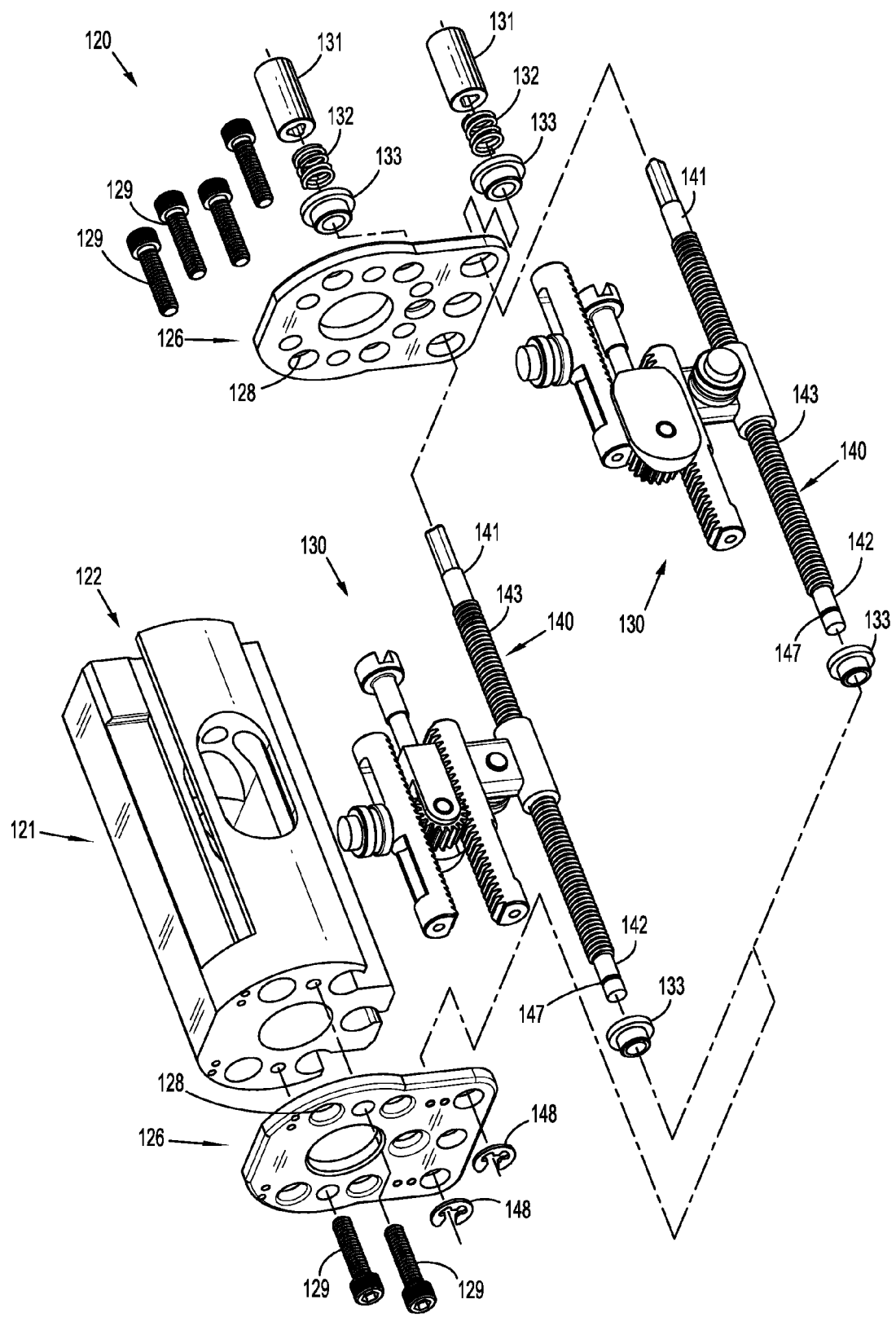
FIG. 4 is a parts-separated view of the control assembly of the surgical articulation assembly as shown in FIG. 1.

Referring to FIG. 4, the control assembly 120 is shown in a parts separated view. Control assembly 120 includes an inner housing 121 and two actuation assemblies 130. Actuation assemblies 130 and associated components are substantially similar, and cooperate to effect articulation of the articulable portion 110 (FIG. 1), as will be described in further detail below. More than two or less than two actuation assemblies 130 may be present in a surgical articulation assembly 100 (FIG. 1) to suit the particular needs of articulation.

Figure 7:
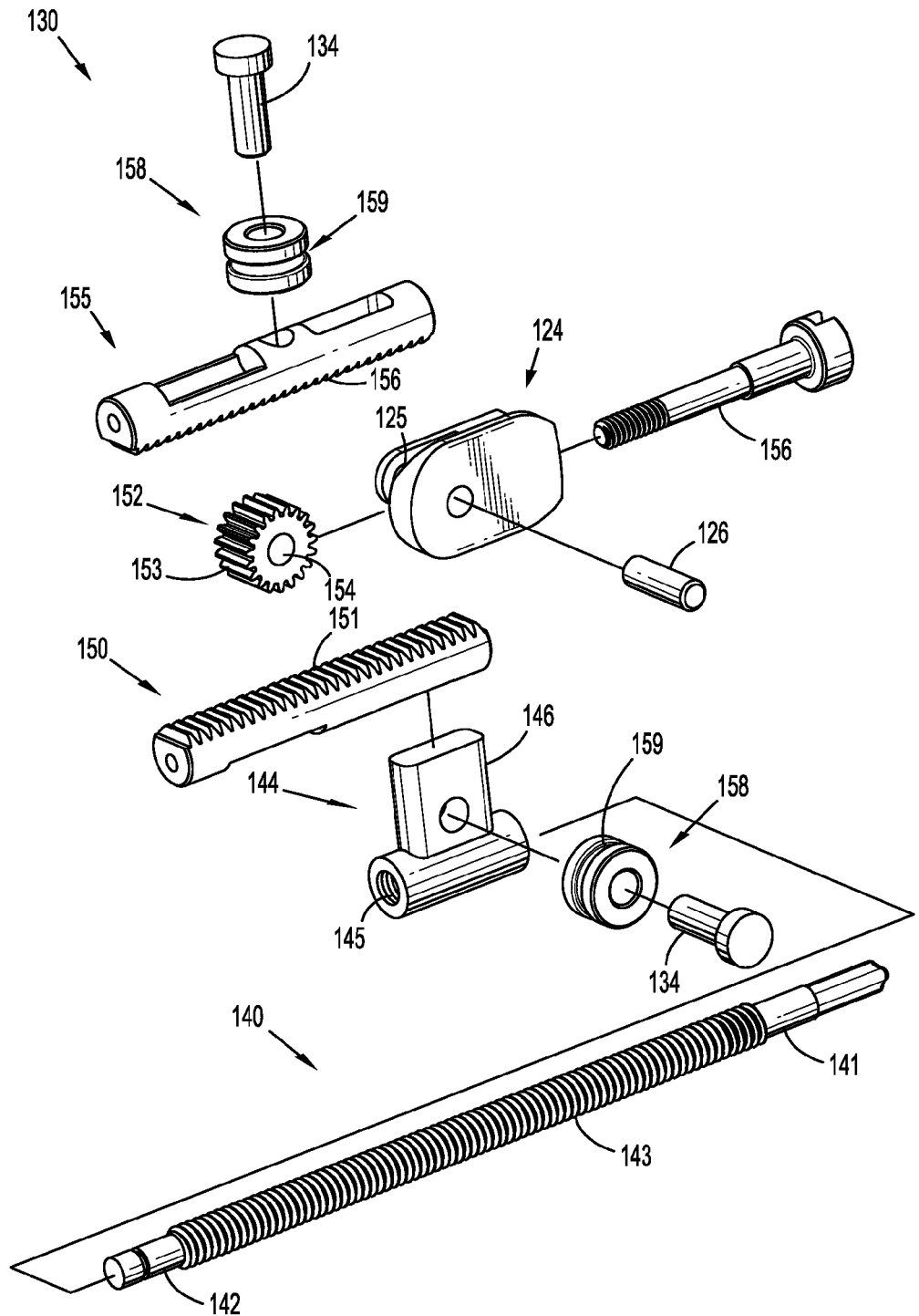
FIG. 7 is a parts-separated view of the actuation assembly of FIG. 6.

Turning for the moment to FIG. 7, an actuation assembly 130 is shown in parts separated view. Actuation assembly 130 includes a driving member 140. Driving member 140 is a longitudinal member that has a proximal portion 141, a distal portion 142, and may have surface features to engage additional components, as will be discussed further below. While driving member 140 is shown here having a threaded surface 143, other surface configurations such as knurls, teeth, grooves, or spokes are contemplated. Driving member 140 rotates about an axis substantially parallel to the longitudinal axis A1 (FIG. 1).

Circumferentially disposed around the driving member 140 is a translating member 144. As shown here, translating member 144 has a cylindrical member configured to be circumferentially disposed on driving members 140. Other shapes and profiles are contemplated for translating member 144. Translating member 144 may contain a channel 145 that is threaded or otherwise textured to engage threaded surface 143 of driving member 140. As the driving member 140 is rotated, the channel 145 will engage the threaded surface 143 of the driving member 140 and the translating member 144 will move proximally and distally along driving member 140. Extending from the translating member 144 is a shoulder 146 that attaches the translating member 144 to a first engaging member 150. Shoulder 146 may be adhered or welded, snap-fit, press fit, or otherwise coupled to first engaging member 150 and translating member 144.

First engaging member 150 is a longitudinal member having a surface 151 for cooperating with other components of the actuation assembly 130, as will be discussed further below. Surface 151 of first engaging member 150 may be grooved, knurled, have ridges or teeth, or may be a toothed rack, as shown here. As the first engaging member 150 is attached to the translating member 144 by way of the shoulder 146, the first engaging member 150 will translate proximally and distally with the translating member 144 as it translates along the driving member 140.

Abutting the first engaging member 150 is a rotating member 152. Rotating member 152 has an outer surface 153 for interengaging the surface 151 of the first engaging member 150. Rotating member 152 may be a pinion having teeth, as shown here, or may be a wheel, have spokes or a frictional surface, or any other suitable surface for engaging surface 151 of first engaging member 150.

Diametrically opposing the first engaging member 150 and abutting the rotating member 152 is a second engaging member 155. Second engaging member 155 is similar to first engaging member 150, and has a surface 156 that interengages the surface 153 of the rotating member 152 in a similar manner. Second engaging member 155 translates in cooperation with the first engaging member 150, as will be discussed further below.

Figure 10:
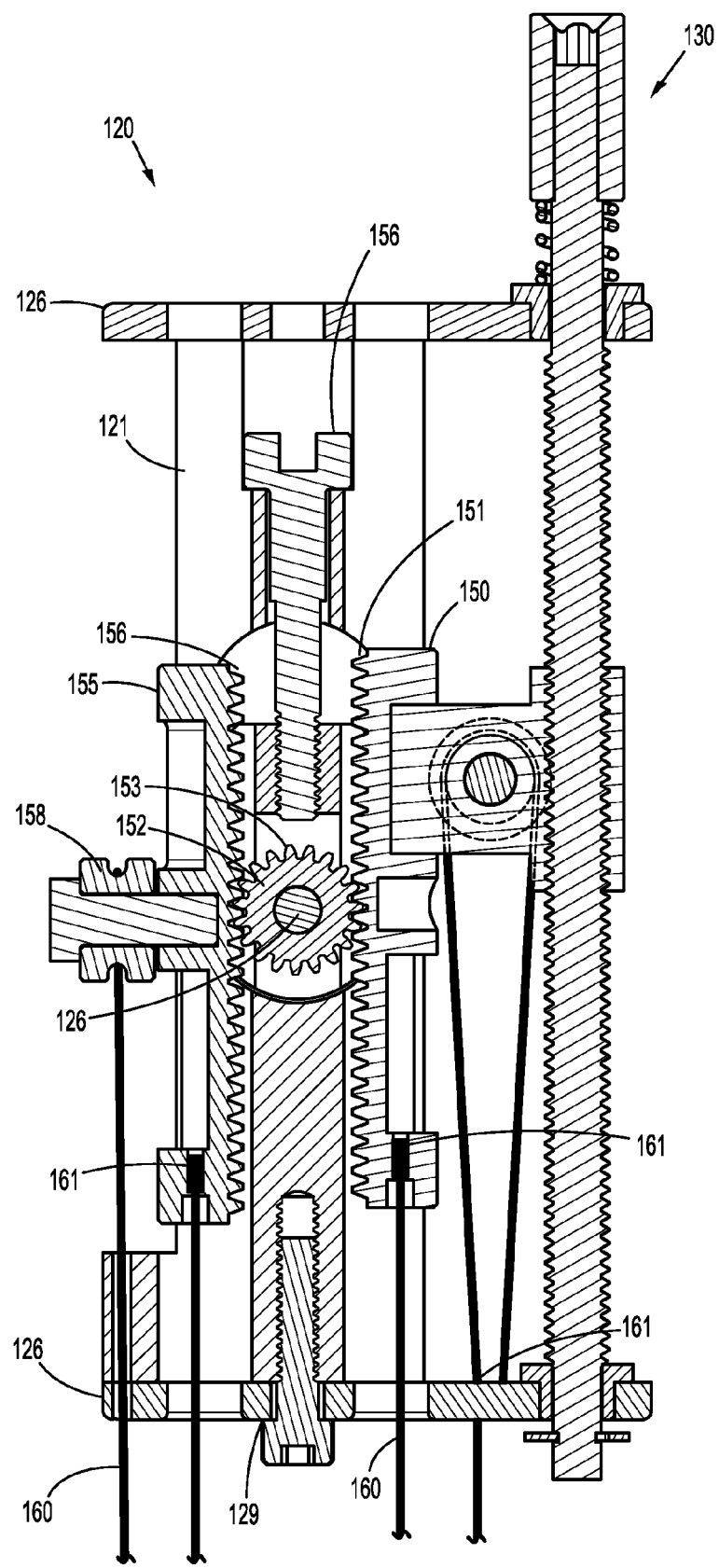
FIG. 10 is a cross-sectional view of the control assembly taken along section line 10-10 of FIG. 9.

Rotating member 152 is disposed in a mount 124. Mount 124 has a recess 125 that receives a portion of rotating member 152, and a pinning member 126 may be disposed through an aperture in the mount 124 and an opening 154 through rotating member 152 such that the rotating member 152 is held in place in the mount 124 and is free to rotate about the pinning member 126. An anchor member 156 may be disposed through a proximal portion of the mount 124 to secure the mount 124 to a portion of the inner housing 121 (FIG. 10). While shown as a rounded, rectangular member, other shapes and profiles are contemplated for mount 124.

Figure 6:
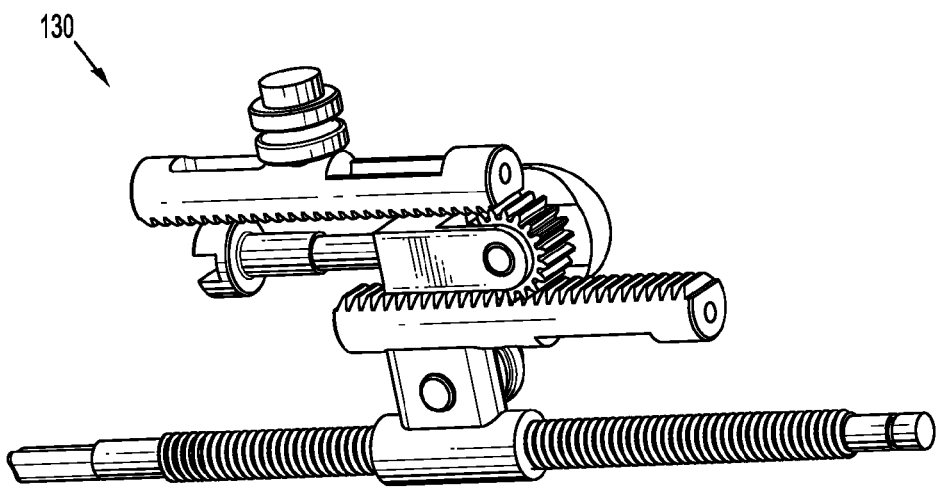
FIG. 6 is a side perspective view of an actuation assembly as shown in FIG. 5, with the connecting members removed.

Attached to an outer surface of each of the first and second engaging members 150, 155 is a pulley 158. Pulley 158 is free to rotate about a securing element 134 that is disposed through each pulley 158 and into each engaging member 150, 155. Securing element 134 may be press fit into an aperture in each engaging member 150, 155, or may be snap fit, welded, adhered, or otherwise coupled. Pulley 158 includes a track 159 to receive a portion of the actuation apparatus 130, as will be described further below. Turning to FIG. 6, the components of the actuation assembly 130 are shown fully assembled.

Figure 5:
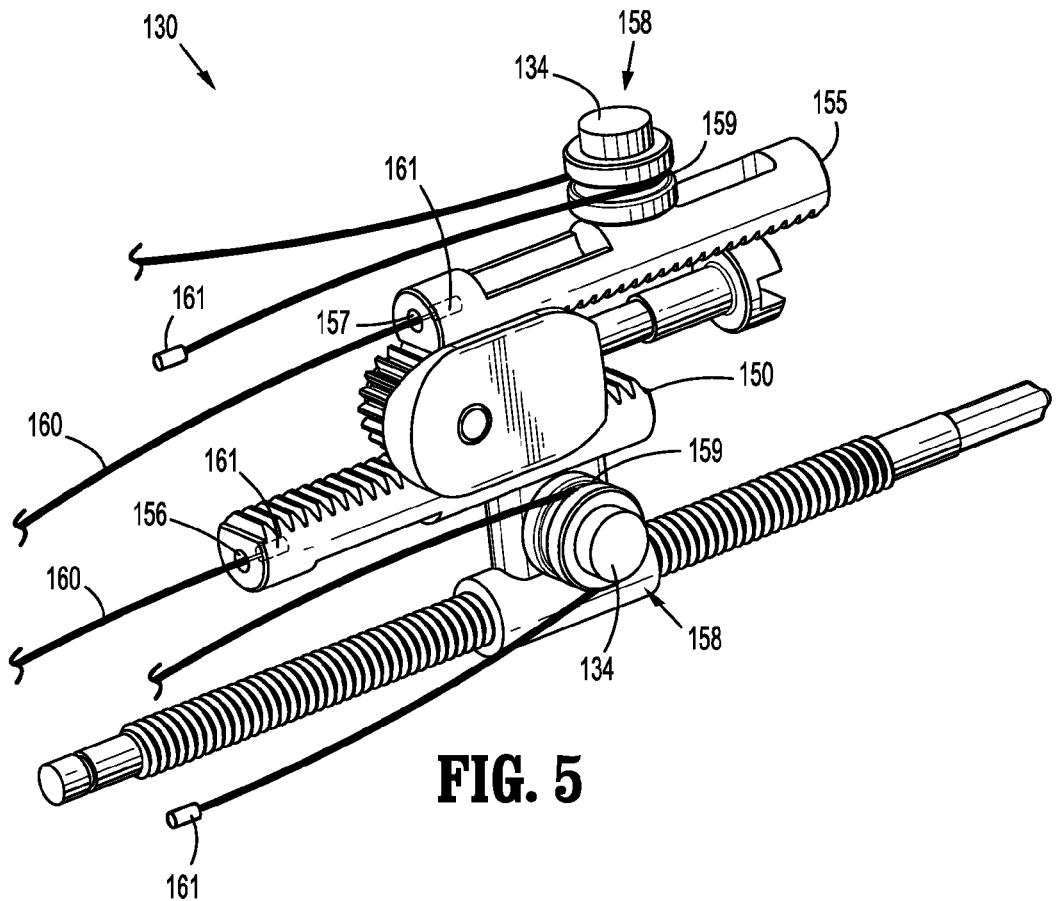
FIG. 5 is an assembled view of an actuation assembly including multiple connecting members.
Figure 14:
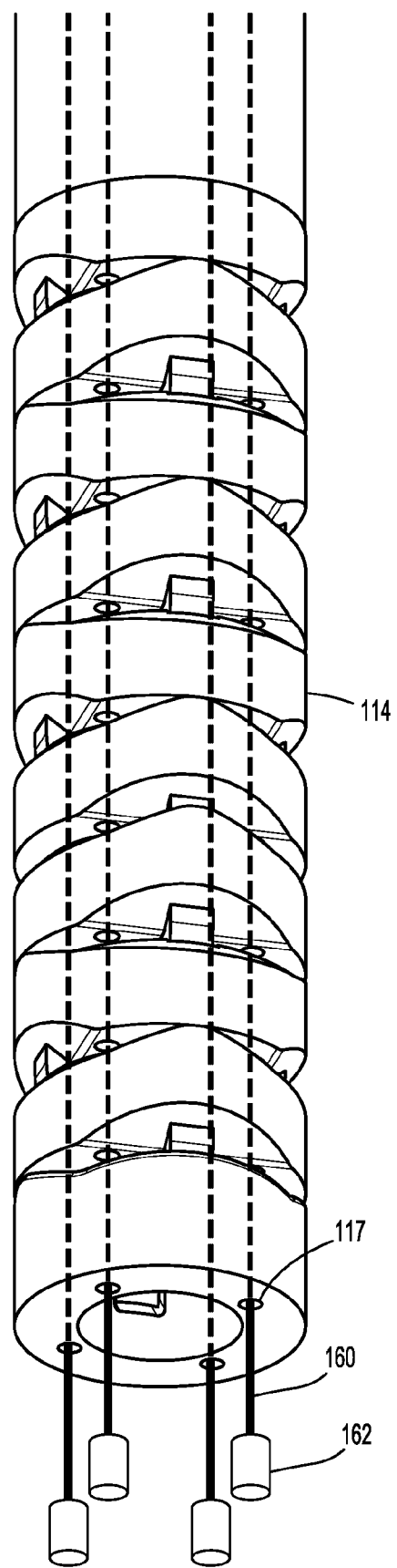
FIG. 14 is an assembled view of a portion of the articulable portion as shown in FIG. 13.

Referring now to FIG. 5, the actuation assembly 130 is shown fully assembled, with connecting members 160 attached to portions the actuation assembly 130. Connecting members 160 couple the actuation apparatus 130 to a portions of the articulable member 110 (FIG. 1). While connecting members 160 are shown as cables, connecting members 160 may be wires or other tensile elements, or may be rigid elements such as bars or links. Connecting members 160 include a proximal end 161 and a distal end 162 (FIG. 14). Ends 161, 162 of the connecting members 160 may be defined by a ferrule as shown, or may be knotted or otherwise defined. Proximal ends 161 are shown disposed in apertures 156, 157 of the first and second engaging members 150, 155, respectively. Connecting members 160 may alternatively be embedded within or adhered to first and second engagement members 150, 155. Connecting members 160 are also shown disposed over a portion of pulleys 158 within track 159. Thus, when pulleys 158 rotate about securing member 134, they displace a portion of connecting members 160 disposed in the track 159.

Referring back to FIG. 4, each actuation assembly 130 is shown in relation to the other components of the control assembly 120. It should be noted that the pair of actuation assemblies 130 shown differ only in that each actuation assembly 130 is configured and oriented to fit in opposing sides of inner housing 121. In embodiments, each actuation assembly may include a driving member 140 with an opposing threaded surface 143. Thus, a first actuation assembly 130 may include a driving member 140 with a right-handed threaded surface 143, and a second actuation assembly 130 may include a driving member 140 with a left-handed threaded surface 143.

Figure 8:
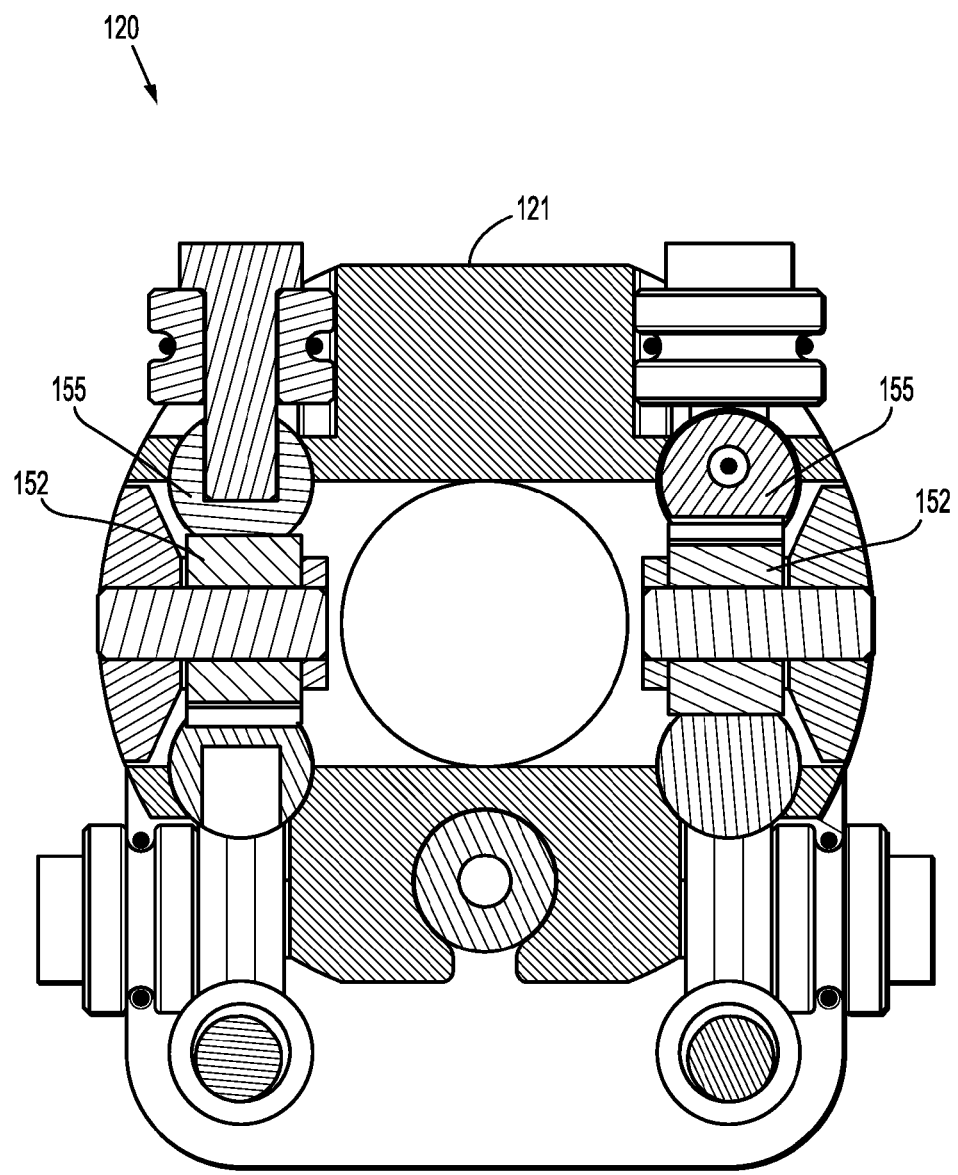
FIG. 8 is a cross-sectional view of the control assembly taken along section line 8-8 of FIG. 2.
Figure 9:
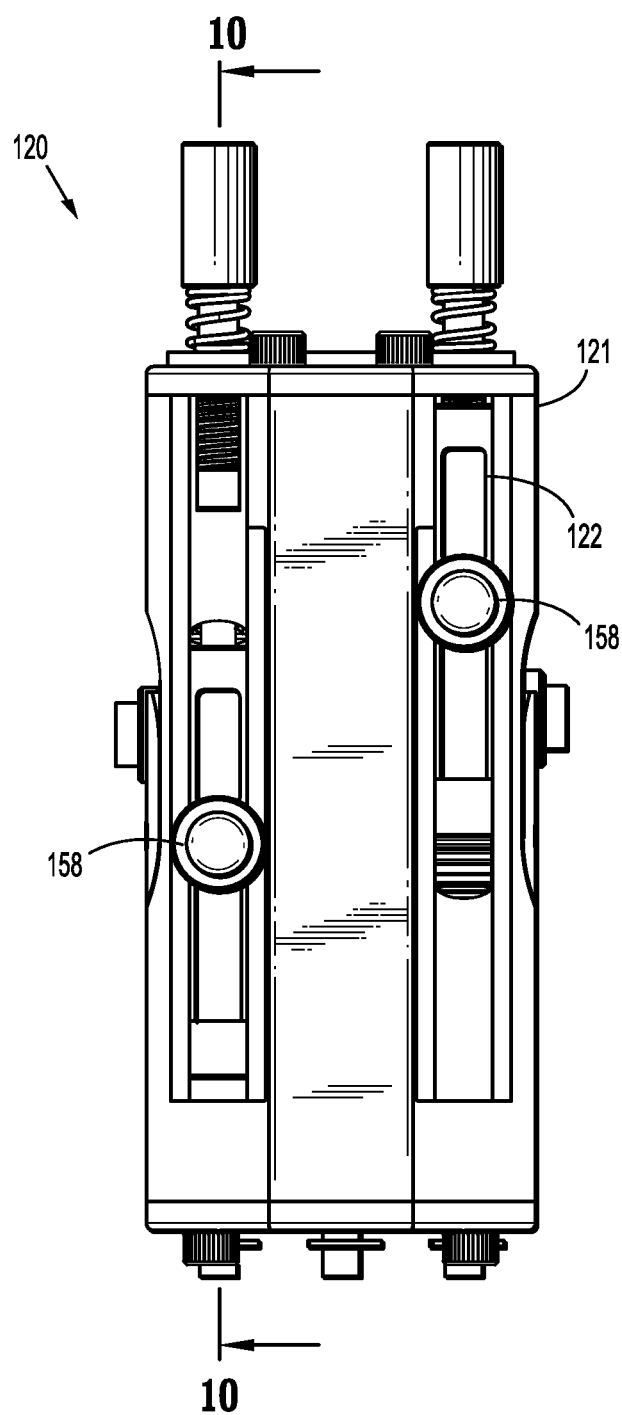
FIG. 9 is a top plan view of a control assembly.

Each actuation assembly 130 is received by recesses 122 formed in the inner housing 121 of the control assembly 120. Recesses 122 are sized and shaped to accommodate the movement and interengagement of the above-described components without interference. Turning momentarily to FIG. 8, a top plan cross-sectional view taken along the line 8-8 (FIG. 2) of the components of the control assembly 120 are shown disposed in the inner housing 121. The second engaging member 155 is disposed in a recess 122 such that the second engaging member 155 is held in position abutting the rotating member 152, and does not separate from this position in the course of operation of the surgical articulation apparatus 100 (FIG. 1). The interengagement of the surface 153 (FIG. 4) of rotating member 152 and surface 156 (FIG. 4) of second engaging member 155 also serves to maintain the second engaging member 155 within the recess 122. The recess 122 does not press the second engaging member 155 such that the translation of the second engaging member 155 through the recess 122 is substantially inhibited during operation of the surgical access assembly 100. Turning momentarily to FIG. 9, a side profile view of the control assembly 120 shows that the pulleys 158 are free to translate proximally and distally within the recesses 122 of inner housing 121.

Turning back to FIG. 4, a pair of mounting plates 126 attach to the inner housing 121, a mounting plate 126 disposed proximally of the inner housing 121, and a mounting plate 126 disposed distally of the inner housing 121. Mounting plates 126 contain a number of apertures 128 that receive portions of the actuation assemblies 130.

The mounting plates 126 receive securing members 129 that extend through apertures 128 and into inner housing 121. As shown here, securing members 129 may be threaded to engage portions of inner housing 121, as best seen with respect to distal mounting plate 126. Proximal portions 141 of driving members 140 extend through recesses 122 of the inner housing 121 and extend through apertures 128 of the proximal mounting plate 126. Proximal portions 141 of driving members 140 are received by user controls 131 that fit an outer surface of proximal portions 141. User controls 131 frictionally engage proximal portions 141 by press fit, interference fit, snap fit, or other suitable coupling, and allow an operator to rotate the driving members 140 from a point proximal of the control assembly 120. Accordingly, user controls 131 may have a ribbed, knurled, or otherwise textured surface to ease manual operation.

A biasing member 132 may be disposed between the proximal mounting plate 126 and the user control 131. The proximal portion 141 of driving member 140 is disposed through the biasing member 132. Biasing member 132, as shown, may be a spring that exerts a biasing force against user control 131 such that the user control 131 is spaced from the mounting plate 126 and does not encounter frictional resistance from the mounting plate 126 during rotation with the driving member 140. The force transmitted proximally against the user control 131 by the biasing member 132 may additionally inhibit distal translation of the driving member 140 through the proximal mounting plate 126.

Mounting caps 133 may be disposed through apertures 128 in the proximal mounting plate 126, to prevent biasing member 132 from extending through aperture 128 and into inner housing 121. Mounting cap 133 also receives the proximal portion 141 of driving member 140 and has a minimal frictional engagement with the proximal portion 141 such that upon rotation, such that driving members 140 encounter minimal frictional resistance from the mounting caps 133 and apertures 128. Accordingly, mounting cap 133 may be formed of a minimally frictional material such as plastics, polymers, or polished metals.

Mounting caps 133 are also disposed in apertures 128 in the distal mounting plate 126, through which distal portions 142 of driving members 140 are disposed. Mounting caps 133 provide minimal frictional resistance against the distal portion 142 of driving member 140, and additionally inhibit the threaded engagement of the threaded surface 143 of driving member 140 with distal mounting plate 126.

Distal portions 142 of driving members 140 also contain a groove 147. A retaining member 148, such as a clip as shown, fits the groove 147, and inhibits the driving members 140 from translating proximally through the distal mounting plate 126 beyond the groove 147. Thus, biasing member 132, mounting caps 133, and retaining member 148 cooperate to maintain the driving members 140 in a substantially stationary axial position in the control assembly 120, such that upon rotation of the user control 131 and driving member 140, the driving member 140 does not translate proximally through the distal mounting plate 126.

Figure 2:
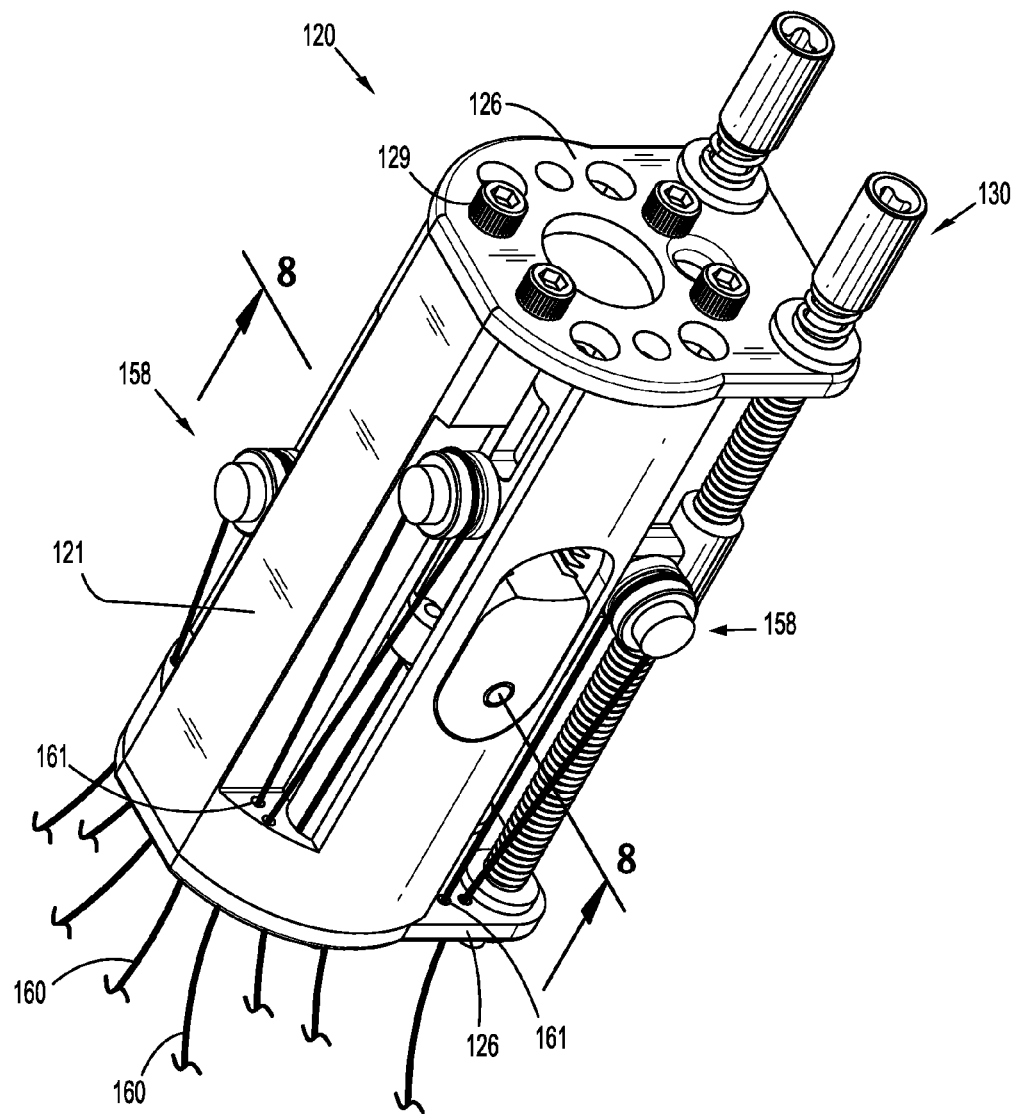
FIG. 2 is a rear perspective view of the control assembly shown in FIG. 1, removed from a housing and including multiple connecting members.
Figure 3:
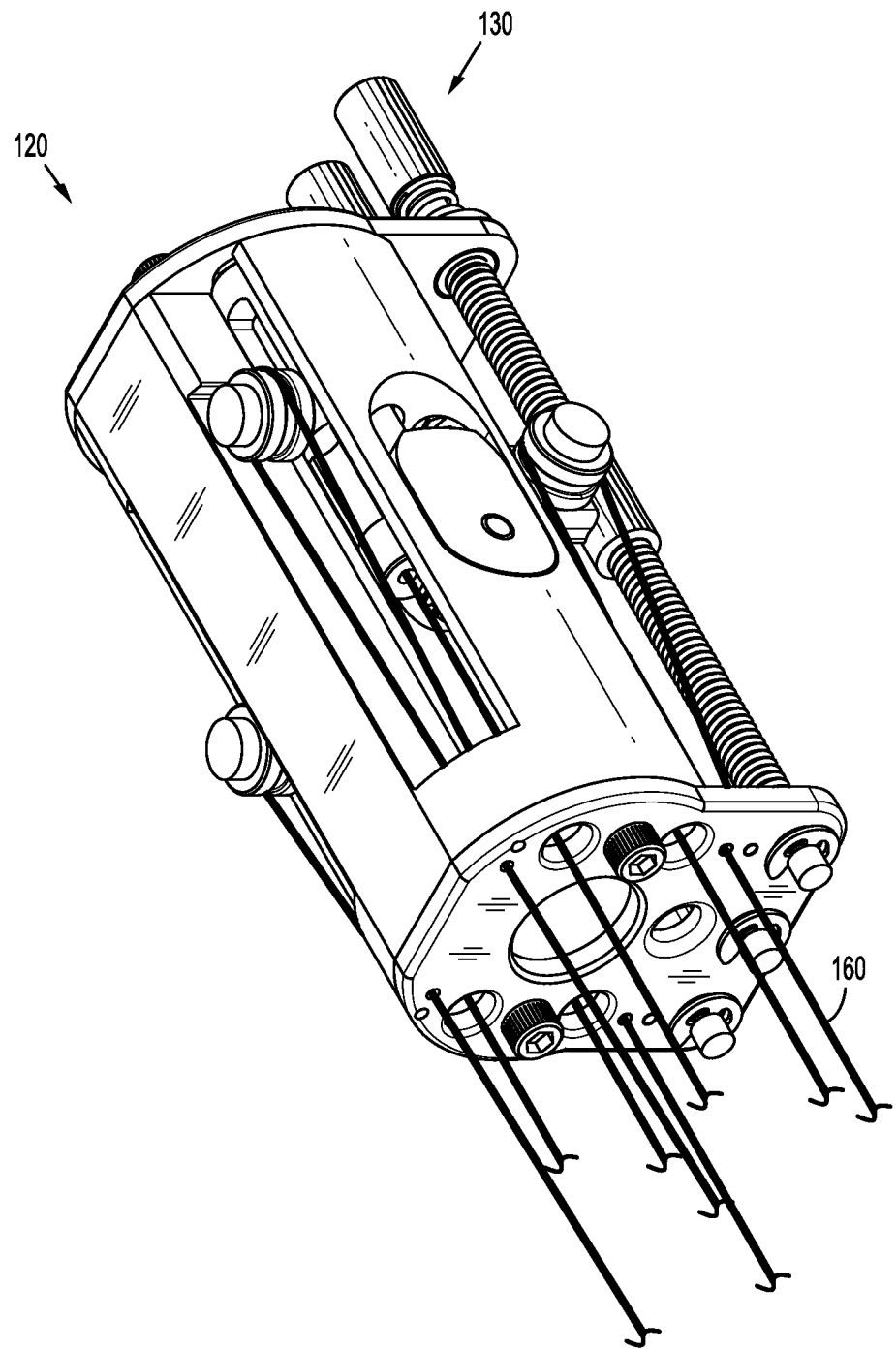
FIG. 3 is a front perspective view of the control assembly and connecting members as seen in FIG. 2

Referring to FIGS. 2 and 10, the control assembly 120 is shown fully assembled. With the mounting plates 126 secured to the inner housing 121 with securing members 129, the components of the actuation assemblies 130 are compressed in a manner such that they will not disengage during use in a minimally invasive procedure. A proximal end 161 of the connecting members 160 associated with the pulleys 158 are attached to a portion of the distal mounting plate 126 as shown. The proximal ends 161 of the connecting members 160 associated with the pulleys 158 may be tied or molded to a portion of mounting plate 126, or may be compressibly engaged by a recess in mounting plate 126 (not shown). Other portions of the connecting members 160 associated with the pulleys 158 may be attached to the mounting plate 126, or another portion of the control assembly 120, elongate member 108, or articulable portion 110 (FIG. 1). Referring to FIG. 3, connecting members 160 are shown extending distally from the control assembly 120 towards articulable portion 110 (FIG. 1). The connecting members 160 associated with each actuation assembly 130 are attached to different portions of the articulable portion 110, as will be discussed further below.

Figure 13:
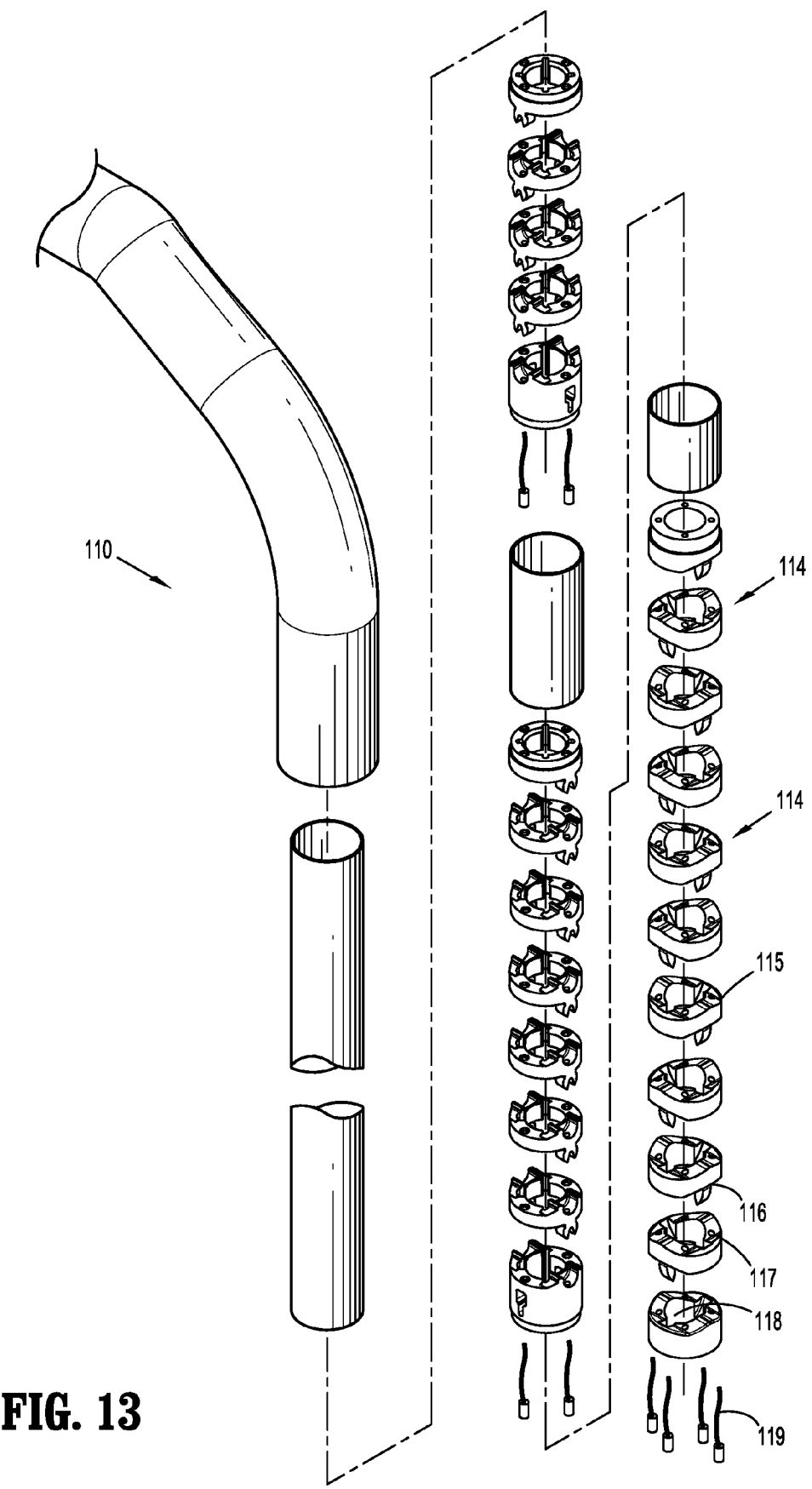
FIG. 13 is a parts separated view of a portion of the articulable portion as shown in FIG. 1.

Referring to FIG. 13, a portion of the articulable portion 110 is shown in parts separated view. The first and second segments 111, 112 (FIG. 1) of the articulable portion may be continuous flexible members, or may include independently movable members 114 that, when assembled, engage in a manner such that each movable member 114 is free to pivot relative to an adjacent movable member 114. Accordingly, movable members 114 contain surface protrusions 115 and surface recesses 116 to engage adjacent movable members 114. Movable members 114 may be connected with connecting elements 119, which may be disposed through an aperture 117 through movable members 114. Connecting elements 119 may be flexible members such as cables or wires, or may be rigid members such as links. As shown, sections of adjacent movable members 114 may have varying surface protrusions 115 and surface recesses 116 such that a series of adjacent movable members 114 is configured for articulation in one direction, and another series of adjacent movable members 114 is configured for articulation in a different direction. Any number and variable configuration of alternating surface protrusions 115 in a series of movable members 114 is contemplated to optimize articulation in multiple planes. Movable members 114 also contain a central aperture 118 bounding a portion of the passage 102 and receiving a portion of surgical object 500 (FIG. 1).

Referring now to FIG. 14, distal ends 162 of connecting members 160 may be disposed through apertures 117 of the distal movable member 114 of a segment 111, 112 (FIG. 1) in addition to or in place of the connecting elements 119 described above (FIG. 7). Alternatively, a distal end 162 may be attached to an internal wall of a segment 111, 112 by adhesion, welding, or looping around an internal structure (not shown). Further, connecting members 160 may be embedded within a surface of articulable portion 110 (not shown).

Figure 11:
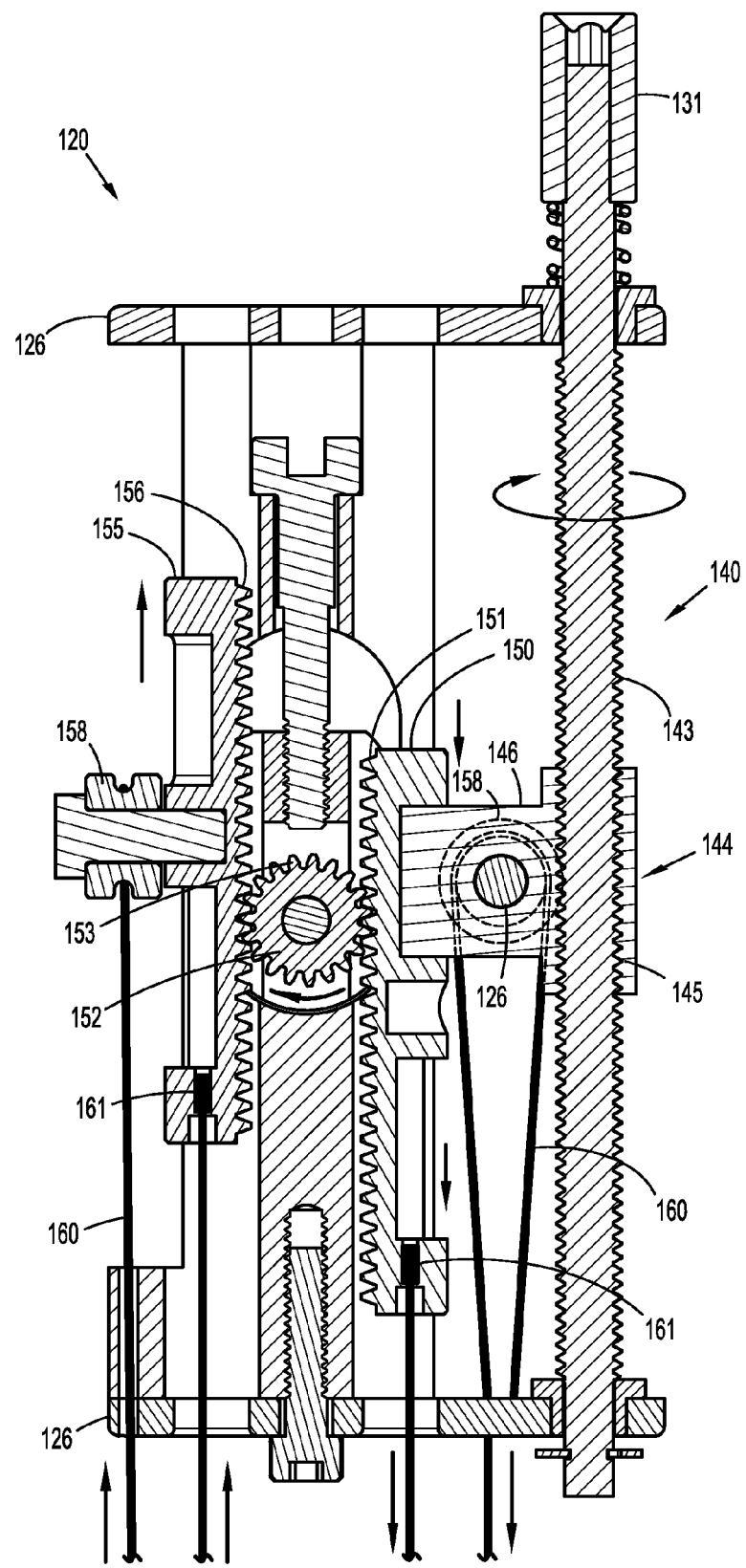
FIG. 11 is the cross-sectional view of a control assembly as seen in FIG. 10, showing the operation of the control assembly.

Turning to FIG. 11, the operation of the control assembly 120 is shown. In use, an operator will rotate one of the user controls 131, causing the driving member 140 to rotate about an axis substantially parallel to the longitudinal axis A1 (FIG. 1). The engagement of the threaded surface 143 with the channel 145 of the translating member 144 will cause the translating member 144 to translate proximally or distally along the driving member 140. As the first engaging member 150 is attached to the translating member 144 with the shoulder 146, the translating member 144 will also translate proximally or distally. Accordingly, the connecting members 160 associated with the pulleys 158 will translate proximally or distally with the simultaneous translation of the first engaging member 150 and the rotation of the pulley 158 about the pinning member 126.

As the first engaging member 150 translates proximally and distally, the surface 151 of the first engaging member 150 interengages the surface 153 of the rotating member 152, causing the rotation of the rotating member 152 about the pinning member 126. As the surface 153 of the rotating member 152 rotates, it interengages the surface 156 of the second engaging member 155, causing the proximal or distal translation of the second engaging member 155. As the proximal ends 161 of the connecting members 160 are attached to the first and second engaging members 150, 155, the attached connecting members 160 will translate proximally and distally with the first and second engaging members 150, 155, exerting a force to the first and second segments 111, 112 (FIG. 1). As the pulleys 158 are attached to the first and second engaging members 150, 155, the attached connecting members 160 will translate with and around the pulleys 158 with the translation of the first and second engaging members 150, 155, exerting a force on the first and second segments 111, 112 (FIG. 12).

Each connecting member 160 attached to the first and second engaging members 150, 155 is attached to an opposing portion of the first segment 111 (FIG. 14), and each connecting member 160 associated with each pulley 158 is attached to opposing surfaces of the second segment 112 (FIG. 14). Accordingly, as the connecting members 160 associated with the first engagement member 150 translate proximally, the connecting members 160 associated with the second engagement member 155 translate distally, and vice-versa. Thus, a pair of axially opposing forces will be exerted on opposing surfaces of the first and second segments 111, 112 through the connecting members 160. Accordingly, the surgical access assembly 100 (FIG. 1) is configured for bi-directional articulation. A second actuation assembly 130 may include connecting members 160 attached at radially spaced points on the first and second segments 111, 112 from those described above. Accordingly, the surgical access assembly 100 may effect bi-directional articulation in more than one plane. Other placements of the connecting members 160 within the first and second segments 111, 112 are contemplated.

As the proximal ends 161 of the connecting members 161 associated with each pulley 158 are attached to a portion of the mounting plate 126, the connecting members 160 associated with pulleys 158 may displace a greater length of the connecting members 160, or exert a different force upon first and second segments 111, 112 upon proximal or distal translation than the connecting members 160 attached to the first and second engaging members 150, 155. Accordingly, the engagement of the actuation apparatus 130 results in greater displacement of the second segment 112 than the first segment 111. The connecting members 160 may be of any length or thickness, and the pulleys 158 may be of any diameter to effect articulation of the second segment 112 at a different rate than the first segment 111. In embodiments, the pulleys 158 will displace the second segment 112 a distance twice that of the distance the first and second engaging members 150, 155 will displace the first segment 111.

Figure 12:
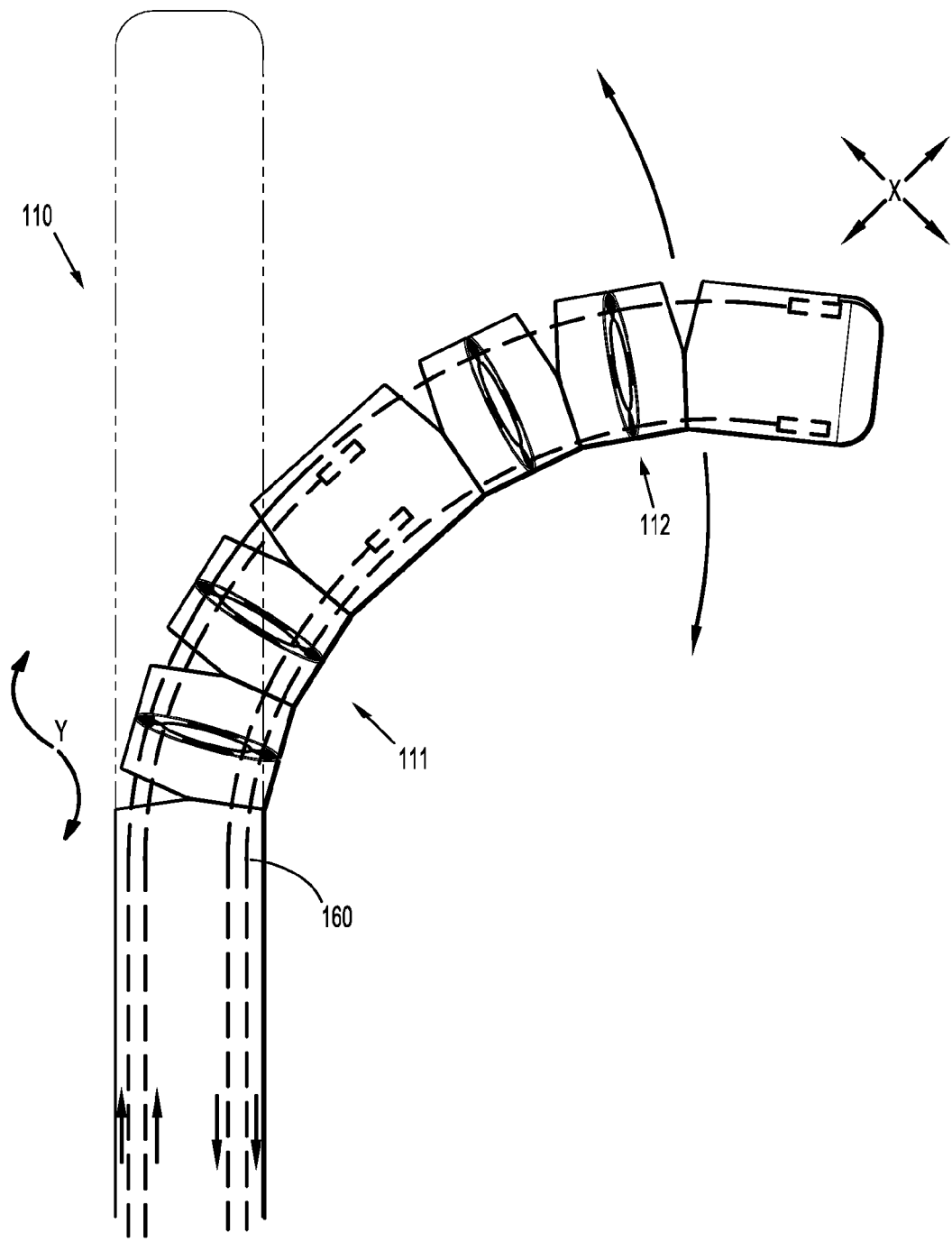
FIG. 12 is an enlarged area of detail view of the first and second segments as shown in FIG. 1, showing bi-directional articulation of the first and second segments in a first plane and a second plane.

Turning to FIG. 12, articulation of the articulable portion 110 is shown. As forces are transmitted to the connecting members 160 (shown in phantom view), displacement of the first and second segments 111, 112 is effected in a first plane, i.e., plane X (across the page) and a second plane, i.e., plane Y (into and out of the page). Connecting members 160 associated with a first actuation assembly 130 (FIG. 4) may be attached to opposing surfaces in each of the first and second segments 111, 112 to effect articulation in plane X, and connecting members 160 associated with a second articulation assembly 130 may be attached to opposing surfaces in each of the first and second segments 111, 112 and radially spaced from the connecting members 160 of the first articulation assembly 130 to effect articulation in plane Y. Forward and reverse engagement of the pair of actuation assemblies 130 allows for bi-directional articulation of the first and second segments 111, 112 in both plane X and plane Y. Accordingly, a surgical object 500 (FIG. 1) inserted through the surgical articulation assembly 100 (FIG. 1) can be articulated in opposing directions in multiple planes.

It will be understood that various modifications may be made to the embodiments disclosed herein. Therefore, the above description should not be construed as limiting, but merely as exemplifications of embodiments. Those skilled in the art will envision other modifications within the scope and spirit of the present disclosure.

What is claimed is:

1. A surgical articulation assembly, comprising:
an elongate member defining a longitudinal axis and having a passage therethrough, a portion of the elongate member having a first segment and a second segment, each segment configured and dimensioned for movement relative to the longitudinal axis, the second segment disposed distally of the first segment;
a first actuation apparatus having a first plurality of connecting members and being operatively coupled to a portion of the first segment and a portion of the second segment, wherein actuation of the first actuation apparatus moves the first segment a first distance and the second segment a second distance in a first plane; and
a second actuation apparatus having a second plurality of connecting members and being operatively coupled to a portion of the first segment and a portion of the second segment, wherein actuation of the second actuation apparatus moves the first segment the first distance and the second segment the second distance in a second plane, wherein at least one of the first or second pluralities of connecting members includes a length associated with a pulley.

2. The surgical articulation assembly of claim 1, wherein the first plane and the second plane are substantially transverse.

3. The surgical articulation assembly of claim 1, wherein the first distance is different than the second distance.

4. The surgical articulation assembly of claim 3, wherein the second distance is twice the first distance.

5. The surgical articulation assembly of claim 1, wherein at least one of the first or second actuation apparatuses includes a rotatable member in mechanical cooperation with a translatable member, one of the first or second pluralities of connecting members attached to a portion of the translatable member.

6. The surgical articulation assembly of claim 1, wherein the length associated with the pulley is attached to a portion of the surgical articulation assembly proximally of the first and second segments.

7. The surgical articulation assembly of claim 1, wherein forward actuation of one of the first or second actuation apparatuses effects motion of the first and second segments in a first direction in one of the first or second planes, and reverse actuation of the one of the first or second actuation apparatuses effects motion in a second direction in the one of the first or second planes.

8. The surgical articulation assembly of claim 7, wherein the first direction is opposite the second direction.

9. The surgical articulation assembly of claim 1, wherein a surgical object is in mechanical communication with the passage.

10. The surgical articulation assembly of claim 1, wherein at least a portion of the elongate member includes independently movable members.

11. The surgical articulation assembly of claim 1, wherein actuation of at least one of the first or second actuation apparatuses exerts a force on the first and second segments through the respective plurality of connecting members.

12. The surgical articulation assembly of claim 1, wherein at least one of the first or second pluralities of connecting members includes connecting members diametrically opposing each other.

13. A method of effecting articulation of a surgical object, comprising:
inserting a surgical articulation assembly into a tissue site, the surgical articulation assembly including:
an elongate member defining a longitudinal axis and having a passage therethrough, a portion of the elongate member having a first segment and a second segment, each segment configured and dimensioned for movement relative to the longitudinal axis, the second segment disposed distally of the first segment;
a first actuation apparatus having a first plurality of connecting members and being operatively coupled to a portion of the first segment and a portion of the second segment; and
a second actuation apparatus having a second plurality of connecting members and being operatively coupled to a portion of the first segment and a portion of the second segment, wherein at least one of the first or second pluralities of connecting members includes a length associated with a pulley;
inserting the surgical object through the passage;
actuating the first actuation apparatus to effect motion of the first segment a first distance in a first plane and motion of the second segment a second distance in the first plane; and
actuating the second actuation apparatus to effect motion of the first segment the first distance in a second plane and motion of the second segment the second distance in the second plane.

14. The method of claim 13, wherein actuating the first actuation apparatus and the second actuation apparatus includes actuating the first actuation apparatus and the second apparatus such that the first plane and the second plane are substantially transverse.

15. The method of claim 13, wherein actuating the first actuation apparatus and the second actuation apparatus includes actuating the first actuation apparatus and the second apparatus such that the first distance is different than the second distance.

16. The method of claim 15, wherein actuating the first actuation apparatus and the second actuation apparatus includes actuating the first actuation apparatus and the second apparatus such that the second distance is twice the first distance.

17. The method of claim 13, further including inserting the surgical access assembly through an access member.

18. The method of claim 13, including actuating one of the first or second actuation apparatuses to move the first and second segments in a first direction in the first plane or a first direction in the second plane.

19. The method of claim 18, including actuating one of the first or second actuation apparatuses in reverse to move the first and second segments in a second direction in the first plane or a second direction in the second plane, the first directions opposite the respective second directions.

\* \* \* \* \*